United States Patent
Sgroi, Jr.

(10) Patent No.: US 11,246,599 B2
(45) Date of Patent: Feb. 15, 2022

(54) END EFFECTOR FOR CIRCULAR STAPLING INSTRUMENT

(71) Applicant: Covidien LP, Mansfield, MA (US)

(72) Inventor: Anthony Sgroi, Jr., Wallingford, CT (US)

(73) Assignee: Covidien LP, Mansfield, MA (US)

( * ) Notice: Subject to any disclaimer, the term of this patent is extended or adjusted under 35 U.S.C. 154(b) by 60 days.

(21) Appl. No.: 16/825,503

(22) Filed: Mar. 20, 2020

(65) Prior Publication Data

US 2020/0337708 A1  Oct. 29, 2020

Related U.S. Application Data

(60) Provisional application No. 62/838,537, filed on Apr. 25, 2019.

(51) Int. Cl.
| | |
|---|---|
| A61B 17/068 | (2006.01) |
| A61B 17/115 | (2006.01) |
| A61B 17/072 | (2006.01) |
| A61B 17/00 | (2006.01) |

(52) U.S. Cl.
CPC . *A61B 17/1155* (2013.01); *A61B 2017/00477* (2013.01); *A61B 2017/07257* (2013.01); *A61B 2017/07271* (2013.01); *A61B 2017/07285* (2013.01)

(58) Field of Classification Search
CPC ............... A61B 17/1155; A61B 2017/07257
See application file for complete search history.

(56) References Cited

U.S. PATENT DOCUMENTS

| | | | |
|---|---|---|---|
| 3,193,165 | A | 7/1965 | Akhalaya et al. |
| 3,388,847 | A | 6/1968 | Kasulin et al. |
| 3,552,626 | A | 1/1971 | Astafiev et al. |
| 3,638,652 | A | 2/1972 | Kelley |
| 3,771,526 | A | 11/1973 | Rudie |
| 4,198,982 | A | 4/1980 | Fortner et al. |
| 4,207,898 | A | 6/1980 | Becht |
| 4,289,133 | A | 9/1981 | Rothfuss |
| 4,304,236 | A | 12/1981 | Conta et al. |
| 4,319,576 | A | 3/1982 | Rothfuss |
| 4,350,160 | A | 9/1982 | Kolesov et al. |
| 4,351,466 | A | 9/1982 | Noiles |
| 4,379,457 | A | 4/1983 | Gravener et al. |
| 4,473,077 | A | 9/1984 | Noiles et al. |
| 4,476,863 | A | 10/1984 | Kanshin et al. |
| 4,485,817 | A | 12/1984 | Swiggett |
| 4,488,523 | A | 12/1984 | Shichman |
| 4,505,272 | A | 3/1985 | Utyamyshev et al. |
| 4,505,414 | A | 3/1985 | Filipi |
| 4,520,817 | A | 6/1985 | Green |
| 4,550,870 | A | 11/1985 | Krumme et al. |

(Continued)

FOREIGN PATENT DOCUMENTS

| | | |
|---|---|---|
| CA | 908529 A | 8/1972 |
| CA | 2805365 A1 | 8/2013 |

(Continued)

*Primary Examiner* — Eyamindae C Jallow (57) ABSTRACT

An end effector for use with a circular stapling instrument incorporates an anvil assembly having features which enhance the coring or cutting of organ tissue internal of the annular array of staples thereby creating a tubular passage free of tissue obstructions.

20 Claims, 8 Drawing Sheets

(56) References Cited

U.S. PATENT DOCUMENTS

| | | | |
|---|---|---|---|
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,632,290 A | 12/1986 | Green et al. |
| 4,646,745 A | 3/1987 | Noiles |
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,717,063 A | 1/1988 | Ebihara |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,873,977 A | 10/1989 | Avant et al. |
| 4,893,662 A | 1/1990 | Gervasi |
| 4,903,697 A | 2/1990 | Resnick et al. |
| 4,907,591 A * | 3/1990 | Vasconcellos ....... A61B 17/115 606/154 |
| 4,917,114 A | 4/1990 | Green et al. |
| 4,957,499 A | 9/1990 | Lipatov et al. |
| 4,962,877 A | 10/1990 | Hervas |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Blanco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,454,825 A | 10/1995 | Van Leeuwen et al. |
| 5,464,415 A | 11/1995 | Chen |
| 5,470,006 A | 11/1995 | Rodak |
| 5,474,223 A | 12/1995 | Viola et al. |
| 5,497,934 A | 3/1996 | Brady et al. |
| 5,503,635 A | 4/1996 | Sauer et al. |
| 5,522,534 A | 6/1996 | Viola et al. |
| 5,533,661 A | 7/1996 | Main et al. |
| 5,588,579 A * | 12/1996 | Schnut ................. A61B 17/115 227/175.1 |
| 5,609,285 A | 3/1997 | Grant et al. |
| 5,626,591 A | 5/1997 | Kockerling et al. |
| 5,632,433 A | 5/1997 | Grant et al. |
| 5,639,008 A | 6/1997 | Gallagher et al. |
| 5,641,111 A | 6/1997 | Ahrens et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |
| 5,799,857 A | 9/1998 | Robertson et al. |
| 5,814,055 A | 9/1998 | Knodel et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A * | 1/1999 | Robertson ........... A61B 17/1114 227/179.1 |
| 5,868,760 A | 2/1999 | McGuckin, Jr. |
| 5,881,943 A | 3/1999 | Heck et al. |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,024,748 A | 2/2000 | Manzo et al. |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,142,933 A | 11/2000 | Longo et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Bittner et al. |
| 6,203,553 B1 | 3/2001 | Robertson et al. |
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 | 7/2001 | Balazs et al. |
| 6,264,086 B1 | 7/2001 | McGuckin, Jr. |
| 6,269,997 B1 | 8/2001 | Balazs et al. |
| 6,273,897 B1 | 8/2001 | Dalessandro et al. |
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |
| 6,387,105 B1 | 5/2002 | Gifford, III et al. |
| 6,398,795 B1 | 6/2002 | McAlister et al. |
| 6,402,008 B1 | 6/2002 | Lucas |
| 6,439,446 B1 | 8/2002 | Perry et al. |
| 6,443,973 B1 | 9/2002 | Whitman |
| 6,450,390 B2 | 9/2002 | Heck et al. |
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |

(56) References Cited

U.S. PATENT DOCUMENTS

| | | |
|---|---|---|
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicolo |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,141,055 B2 | 11/2006 | Abrams et al. |
| 7,168,604 B2 | 1/2007 | Milliman et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,125 B2 | 10/2007 | Viola |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 | 4/2008 | Milliman |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 * | 10/2008 | Milliman ............ A61B 17/068 227/178.1 |
| 7,438,718 B2 | 10/2008 | Milliman et al. |
| 7,455,676 B2 | 11/2008 | Holsten et al. |
| 7,455,682 B2 | 11/2008 | Viola |
| 7,481,347 B2 | 1/2009 | Roy |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,540,839 B2 | 6/2009 | Butler et al. |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma et al. |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,712 B2 | 9/2010 | Milliman et al. |
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Milliman |
| 7,886,951 B2 | 2/2011 | Hessler |
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |
| 7,918,377 B2 | 4/2011 | Measamer et al. |
| 7,922,062 B2 | 4/2011 | Cole et al. |
| 7,922,743 B2 | 4/2011 | Heinrich et al. |
| 7,931,183 B2 | 4/2011 | Orban, III |
| 7,938,307 B2 | 5/2011 | Bettuchi |
| 7,942,302 B2 | 5/2011 | Roby et al. |
| 7,951,166 B2 | 5/2011 | Orban, III et al. |
| 7,959,050 B2 | 6/2011 | Smith et al. |
| 7,967,181 B2 | 6/2011 | Viola et al. |
| 7,975,895 B2 | 7/2011 | Milliman |
| 8,002,795 B2 | 8/2011 | Beetel |
| 8,006,701 B2 | 8/2011 | Bilotti et al. |
| 8,006,889 B2 | 8/2011 | Adams et al. |
| 8,011,551 B2 | 9/2011 | Marczyk et al. |
| 8,011,554 B2 | 9/2011 | Milliman |

(56) References Cited

U.S. PATENT DOCUMENTS

| | | |
|---|---|---|
| 8,016,177 B2 | 9/2011 | Bettuchi et al. |
| 8,016,858 B2 | 9/2011 | Whitman |
| 8,020,741 B2 | 9/2011 | Cole et al. |
| 8,025,199 B2 | 9/2011 | Whitman et al. |
| 8,028,885 B2 | 10/2011 | Smith et al. |
| 8,038,046 B2 | 10/2011 | Smith et al. |
| 8,043,207 B2 | 10/2011 | Adams |
| 8,066,167 B2 | 11/2011 | Measamer et al. |
| 8,066,169 B2 | 11/2011 | Viola |
| 8,070,035 B2 | 12/2011 | Holsten et al. |
| 8,070,037 B2 | 12/2011 | Csiky |
| 8,096,458 B2 | 1/2012 | Hessler |
| 8,109,426 B2 | 2/2012 | Milliman et al. |
| 8,109,427 B2 | 2/2012 | Orban, III |
| 8,113,405 B2 | 2/2012 | Milliman |
| 8,113,406 B2 | 2/2012 | Holsten et al. |
| 8,113,407 B2 | 2/2012 | Holsten et al. |
| 8,123,103 B2 | 2/2012 | Milliman |
| 8,128,645 B2 | 3/2012 | Sonnenschein et al. |
| 8,132,703 B2 | 3/2012 | Milliman et al. |
| 8,136,712 B2 | 3/2012 | Zingman |
| 8,146,790 B2 | 4/2012 | Milliman |
| 8,146,791 B2 | 4/2012 | Bettuchi et al. |
| 8,181,838 B2 | 5/2012 | Milliman et al. |
| 8,192,460 B2 | 6/2012 | Orban, III et al. |
| 8,201,720 B2 | 6/2012 | Hessler |
| 8,203,782 B2 | 6/2012 | Brueck et al. |
| 8,211,130 B2 | 7/2012 | Viola |
| 8,225,799 B2 | 7/2012 | Bettuchi |
| 8,225,981 B2 | 7/2012 | Criscuolo et al. |
| 8,231,041 B2 | 7/2012 | Marczyk et al. |
| 8,231,042 B2 | 7/2012 | Hessler et al. |
| 8,257,391 B2 | 9/2012 | Orban, III et al. |
| 8,267,301 B2 | 9/2012 | Milliman et al. |
| 8,272,552 B2 | 9/2012 | Holsten et al. |
| 8,276,802 B2 | 10/2012 | Kostrzewski |
| 8,281,975 B2 | 10/2012 | Criscuolo et al. |
| 8,286,845 B2 | 10/2012 | Perry et al. |
| 8,308,045 B2 | 11/2012 | Bettuchi et al. |
| 8,312,885 B2 | 11/2012 | Bettuchi et al. |
| 8,313,014 B2 | 11/2012 | Bettuchi |
| 8,317,073 B2 | 11/2012 | Milliman et al. |
| 8,317,074 B2 | 11/2012 | Ortiz et al. |
| 8,322,590 B2 | 12/2012 | Patel et al. |
| 8,328,060 B2 | 12/2012 | Jankowski et al. |
| 8,328,062 B2 | 12/2012 | Viola |
| 8,328,063 B2 | 12/2012 | Milliman et al. |
| 8,343,185 B2 | 1/2013 | Milliman et al. |
| 8,353,438 B2 | 1/2013 | Baxter, III et al. |
| 8,353,439 B2 | 1/2013 | Baxter, III et al. |
| 8,353,930 B2 | 1/2013 | Heinrich et al. |
| 8,360,295 B2 | 1/2013 | Milliman et al. |
| 8,365,974 B2 | 2/2013 | Milliman |
| 8,403,942 B2 | 3/2013 | Milliman et al. |
| 8,408,441 B2 | 4/2013 | Wenchell et al. |
| 8,413,870 B2 | 4/2013 | Pastorelli et al. |
| 8,413,872 B2 | 4/2013 | Patel |
| 8,418,905 B2 | 4/2013 | Milliman |
| 8,418,909 B2 | 4/2013 | Kostrzewski |
| 8,424,535 B2 | 4/2013 | Hessler et al. |
| 8,424,741 B2 | 4/2013 | McGuckin, Jr. et al. |
| 8,430,291 B2 | 4/2013 | Heinrich et al. |
| 8,430,292 B2 | 4/2013 | Patel et al. |
| 8,453,910 B2 | 6/2013 | Bettuchi et al. |
| 8,453,911 B2 | 6/2013 | Milliman et al. |
| 8,485,414 B2 | 7/2013 | Criscuolo et al. |
| 8,490,853 B2 | 7/2013 | Criscuolo et al. |
| 8,511,533 B2 | 8/2013 | Viola et al. |
| 8,551,138 B2 | 10/2013 | Orban, III et al. |
| 8,567,655 B2 | 10/2013 | Nalagatla et al. |
| 8,579,178 B2 | 11/2013 | Holsten et al. |
| 8,590,763 B2 | 11/2013 | Milliman |
| 8,590,764 B2 | 11/2013 | Hartwick et al. |
| 8,608,047 B2 | 12/2013 | Holsten et al. |
| 8,616,428 B2 | 12/2013 | Milliman et al. |
| 8,616,429 B2 | 12/2013 | Viola |
| 8,622,275 B2 | 1/2014 | Baxter, III et al. |
| 8,631,993 B2 | 1/2014 | Kostrzewski |
| 8,636,187 B2 | 1/2014 | Hueil et al. |
| 8,640,940 B2 | 2/2014 | Ohdaira |
| 8,662,370 B2 | 3/2014 | Takei |
| 8,663,258 B2 | 3/2014 | Bettuchi et al. |
| 8,672,931 B2 | 3/2014 | Goldboss et al. |
| 8,678,264 B2 | 3/2014 | Racenet et al. |
| 8,684,248 B2 | 4/2014 | Milliman |
| 8,684,250 B2 | 4/2014 | Bettuchi et al. |
| 8,684,251 B2 | 4/2014 | Rebuffat et al. |
| 8,684,252 B2 | 4/2014 | Patel et al. |
| 8,733,611 B2 | 5/2014 | Milliman |
| 9,782,173 B2 * | 10/2017 | Mozdzierz ....... A61B 17/07292 |
| 2003/0111507 A1 | 6/2003 | Nunez |
| 2004/0073090 A1 | 4/2004 | Butler et al. |
| 2005/0051597 A1 | 3/2005 | Toledano |
| 2005/0107813 A1 | 5/2005 | Gilete Garcia |
| 2006/0000869 A1 | 1/2006 | Fontayne |
| 2006/0011698 A1 | 1/2006 | Okada et al. |
| 2006/0201989 A1 | 9/2006 | Ojeda |
| 2007/0027473 A1 | 2/2007 | Vresh et al. |
| 2007/0029363 A1 | 2/2007 | Popov |
| 2007/0060952 A1 | 3/2007 | Roby et al. |
| 2009/0236392 A1 | 9/2009 | Cole et al. |
| 2009/0236398 A1 | 9/2009 | Cole et al. |
| 2009/0236401 A1 | 9/2009 | Cole et al. |
| 2010/0019016 A1 | 1/2010 | Edoga et al. |
| 2010/0051668 A1 | 3/2010 | Milliman et al. |
| 2010/0084453 A1 | 4/2010 | Hu |
| 2010/0147923 A1 | 6/2010 | D'Agostino et al. |
| 2010/0163598 A1 | 7/2010 | Belzer |
| 2010/0224668 A1 | 9/2010 | Fontayne et al. |
| 2010/0230465 A1 | 9/2010 | Smith et al. |
| 2010/0258611 A1 | 10/2010 | Smith et al. |
| 2010/0264195 A1 | 10/2010 | Bettuchi |
| 2010/0327041 A1 | 12/2010 | Milliman et al. |
| 2011/0011916 A1 | 1/2011 | Levine |
| 2011/0114697 A1 | 5/2011 | Baxter, III et al. |
| 2011/0114700 A1 | 5/2011 | Baxter, III et al. |
| 2011/0144640 A1 | 6/2011 | Heinrich et al. |
| 2011/0147432 A1 | 6/2011 | Heinrich et al. |
| 2011/0192882 A1 | 8/2011 | Hess et al. |
| 2012/0145755 A1 | 6/2012 | Kahn |
| 2012/0193395 A1 | 8/2012 | Pastorelli et al. |
| 2012/0193398 A1 | 8/2012 | Williams et al. |
| 2012/0232339 A1 | 9/2012 | Csiky |
| 2012/0273548 A1 | 11/2012 | Ma et al. |
| 2012/0325888 A1 | 12/2012 | Qiao et al. |
| 2013/0015232 A1 | 1/2013 | Smith et al. |
| 2013/0020372 A1 | 1/2013 | Jankowski et al. |
| 2013/0020373 A1 | 1/2013 | Smith et al. |
| 2013/0032628 A1 | 2/2013 | Li et al. |
| 2013/0056516 A1 | 3/2013 | Viola |
| 2013/0060258 A1 | 3/2013 | Giacomantonio |
| 2013/0092720 A1 * | 4/2013 | Williams ............. A61B 17/115 227/181.1 |
| 2013/0105544 A1 | 5/2013 | Mozdzierz et al. |
| 2013/0105546 A1 | 5/2013 | Milliman et al. |
| 2013/0105551 A1 | 5/2013 | Zingman |
| 2013/0126580 A1 | 5/2013 | Smith et al. |
| 2013/0153630 A1 | 6/2013 | Miller et al. |
| 2013/0153631 A1 | 6/2013 | Vasudevan et al. |
| 2013/0153633 A1 | 6/2013 | Casasanta, Jr. et al. |
| 2013/0153634 A1 | 6/2013 | Carter et al. |
| 2013/0153638 A1 | 6/2013 | Carter et al. |
| 2013/0153639 A1 | 6/2013 | Hodgkinson et al. |
| 2013/0175315 A1 | 7/2013 | Milliman |
| 2013/0175318 A1 | 7/2013 | Felder et al. |
| 2013/0175319 A1 | 7/2013 | Felder et al. |
| 2013/0175323 A1 | 7/2013 | Mandakolathur Vasudevan et al. |
| 2013/0181035 A1 | 7/2013 | Milliman |
| 2013/0181036 A1 | 7/2013 | Olson et al. |
| 2013/0186930 A1 | 7/2013 | Wenchell et al. |
| 2013/0193185 A1 | 8/2013 | Patel |
| 2013/0193187 A1 | 8/2013 | Milliman |
| 2013/0193190 A1 | 8/2013 | Carter et al. |
| 2013/0193191 A1 | 8/2013 | Stevenson et al. |

(56) References Cited

U.S. PATENT DOCUMENTS

| | | |
|---|---|---|
| 2013/0193192 A1 | 8/2013 | Casasanta, Jr. et al. |
| 2013/0200131 A1 | 8/2013 | Racenet et al. |
| 2013/0206816 A1 | 8/2013 | Penna |
| 2013/0214027 A1 | 8/2013 | Hessler et al. |
| 2013/0214028 A1 | 8/2013 | Patel et al. |
| 2013/0228609 A1 | 9/2013 | Kostrzewski |
| 2013/0240597 A1 | 9/2013 | Milliman et al. |
| 2013/0240600 A1 | 9/2013 | Bettuchi |
| 2013/0248581 A1 | 9/2013 | Smith et al. |
| 2013/0277411 A1 | 10/2013 | Hodgkinson et al. |
| 2013/0277412 A1 | 10/2013 | Gresham et al. |
| 2013/0284792 A1 | 10/2013 | Ma |
| 2013/0292449 A1 | 11/2013 | Bettuchi et al. |
| 2013/0299553 A1 | 11/2013 | Mozdzierz |
| 2013/0299554 A1 | 11/2013 | Mozdzierz |
| 2013/0306701 A1 | 11/2013 | Olson |
| 2013/0306707 A1 | 11/2013 | Viola et al. |
| 2014/0008413 A1 | 1/2014 | Williams |
| 2014/0012317 A1 | 1/2014 | Orban et al. |
| 2014/0252062 A1* | 9/2014 | Mozdzierz ....... A61B 17/07292 227/175.1 |
| 2016/0143641 A1 | 5/2016 | Sapienza et al. |
| 2016/0157856 A1 | 6/2016 | Williams et al. |
| 2016/0174988 A1 | 6/2016 | D'Agostino et al. |
| 2016/0302792 A1 | 10/2016 | Motai |
| 2018/0206846 A1* | 7/2018 | Guerrera ............ A61B 17/1155 |

FOREIGN PATENT DOCUMENTS

| | | |
|---|---|---|
| DE | 1057729 B | 5/1959 |
| DE | 3301713 A1 | 7/1984 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 1354560 A2 | 10/2003 |
| EP | 2138118 A2 | 12/2009 |
| EP | 2168510 A1 | 3/2010 |
| EP | 2238926 A2 | 10/2010 |
| EP | 2524656 A2 | 11/2012 |
| FR | 1136020 A | 5/1957 |
| FR | 1461464 A | 2/1966 |
| FR | 1588250 A | 4/1970 |
| FR | 2443239 A1 | 7/1980 |
| GB | 1185292 A | 3/1970 |
| GB | 2016991 A | 9/1979 |
| GB | 2070499 A | 9/1981 |
| JP | 2004147969 A | 5/2004 |
| JP | 2013138860 A | 7/2013 |
| NL | 7711347 A | 4/1979 |
| SU | 1509052 A1 | 9/1989 |
| WO | 8706448 A1 | 11/1987 |
| WO | 8900406 A1 | 1/1989 |
| WO | 9006085 A1 | 6/1990 |
| WO | 98/35614 A1 | 8/1998 |
| WO | 0154594 A1 | 8/2001 |
| WO | 2008107918 A1 | 9/2008 |

* cited by examiner

END EFFECTOR FOR CIRCULAR STAPLING INSTRUMENT

CROSS-REFERENCE TO RELATED APPLICATIONS

This application claims the benefit of and priority to U.S. Provisional Patent Application Ser. No. 62/838,537 filed Apr. 25, 2019, the entire disclosure of which is incorporated by reference herein.

BACKGROUND

1. Technical Description

The present disclosure generally relates to a surgical circular stapling instrument and, more particularly, relates to an end effector for use with a circular stapling instrument and incorporating an anvil assembly having enhanced features which facilitate coring of the joined tissue upon firing of the instrument.

2. Background of Related Art

Surgical stapling instruments for performing surgical procedures such as anastomoses, hemorrhoidectomies, and mucosectomies are well known. In a circular anastomosis procedure, two ends of organ sections are joined with a circular stapling instrument. Typically, these circular stapling instruments include a handle, an elongated shaft with a staple holding component, and an anvil assembly mountable to the staple holding component. The anvil assembly includes an anvil center rod and an attached anvil head which may be pivotal relative to the anvil center rod to facilitate insertion and removal relative to the organ sections. In use, the opposed tissue end margins of the organ sections are clamped between the anvil head and the staple holding component. The instrument is fired which drives an annular array of staples from the staple holding component through the tissue end margins of the organ sections for deformation against the anvil head. An annular knife within the staple holding component is advanced to core or remove organ tissue interior of the staples to clear the internal tubular passage. An example of an instrument for performing circular anastomosis of tissue is disclosed in commonly assigned U.S. Patent Publication No. 2015/0014393, the entire contents of which is incorporated by reference herein.

SUMMARY

The present disclosure is directed to further improvements in anvil assemblies of end effectors for use with circular stapling instruments by incorporating features which, in concert with the annular knife of the stapling instrument, enhances the coring or cutting of organ tissue internal of the annular array of staples thereby creating a tubular passage completely free of tissue obstructions. In one exemplary embodiment, an end effector for use with a circular stapling instrument includes a staple cartridge assembly and an anvil assembly which is mountable relative to the staple cartridge assembly. The staple cartridge assembly includes an annular knife configured for advancing movement from an unactuated position to an actuated position. The anvil assembly includes an anvil center rod and an anvil head coupled to the anvil center rod. The anvil head includes an anvil housing defining a central longitudinal axis and a support disposed within the anvil housing. The support is configured for longitudinal movement relative to the anvil housing from an initial longitudinal position to an advanced longitudinal position upon movement of the annular knife toward the actuated position. The support is configured to rotate through a predetermined angular sector of rotation about the central longitudinal axis upon movement to the advanced longitudinal position to facilitate severing of tissue disposed between the annular knife and the support.

In embodiments, the support includes a backup member having at least one cam member which is engageable with the anvil housing to cause rotation of the support through the predetermined angular sector of rotation. In some embodiments, the anvil housing includes a distal housing wall having at least one cam recess whereby the at least one cam member of the backup member cooperates with the at least one cam recess to cause rotation of the support through the predetermined angular sector of rotation. In certain embodiments, the backup member includes a plurality of cam members depending from a distal face thereof and the housing wall of the anvil housing defines a plurality of cam recesses where individual cam members cooperate with respective individual cam recesses to rotate the support through the predetermined angular sector of rotation. In embodiments, the cam members of the backup member and the cam recesses of the housing wall of the anvil housing are radially spaced with respect to the central longitudinal axis.

In some embodiments, the support also includes a cut ring positioned to be engaged by the annular knife upon movement of the annular knife toward the actuated position. In certain embodiments, the cut ring is coupled to the backup member such that rotation of the backup member causes corresponding rotation of the cut ring. In embodiments, the cut ring is configured to be at least partially penetrated by the annular knife upon movement of the annular knife toward the actuated position.

In certain embodiments, a retainer member is positioned in the anvil housing between the backup member and the housing wall. The retainer member is configured to deform when subjected to a force exerted by the annular knife on the support upon movement of the annular knife to the actuated position thereby permitting longitudinal advancement of the support to the advanced longitudinal position.

In embodiments, the support is fixed from rotational movement about the central longitudinal axis when in the initial longitudinal position. In some embodiments, the anvil head includes an anvil post depending from the housing wall, wherein the retainer, the backup member and the cut ring are coaxially mounted about the anvil post. In certain embodiments, the anvil post includes at least one keyed slot and the backup member includes a corresponding at least one finger. The at least one finger is received within the at least one keyed slot when in the initial longitudinal position of the support thereby preventing rotational movement of the support, and is released from the at least one keyed slot when in the advanced longitudinal position of the support thereby permitting rotational movement of the support. In embodiments, the anvil post includes a pair of diametrically opposed keyed slots and the backup member includes a pair of corresponding diametrically opposed fingers.

In certain embodiments, the anvil head is pivotally mounted to the anvil center rod, and is pivotal from a first operative condition in which the anvil head is in opposition to the staple cartridge assembly to a second tilted condition.

Other features of the present disclosure will be appreciated from the following description.

BRIEF DESCRIPTION OF THE DRAWINGS

Various embodiments of the presently disclosed end effector including an anvil assembly for use with a surgical circular stapling instrument are described herein below with reference to the drawings, wherein.

DETAILED DESCRIPTION OF EMBODIMENTS

Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" refers to that portion of the device or component thereof that is closest to the clinician and the term "distal" refers to that portion of device or component thereof that is farthest from the clinician.

The exemplary surgical stapling instrument includes a handle assembly, an elongate body or adapter extending from the handle assembly, and an end effector couplable to the adapter. The end effector includes a staple cartridge assembly having an annular array of staples and an annular knife, and an anvil assembly. The anvil assembly includes an anvil center rod releasably couplable to the staple cartridge assembly and an anvil head which is pivotally coupled to the anvil center rod. The anvil head includes an anvil housing which accommodates a support and a deformable or frangible retainer disposed distal of the support. The support includes a backup member and a cut ring which is coupled to the backup member. These components maintain the anvil head in an operative condition in opposition to the staple cartridge assembly prior to firing of the instrument. In use, the tissue end margins of the tubular organ sections to be joined are positioned about the anvil head and the staple cartridge assembly, respectively. The anvil head and the staple cartridge assembly are approximated, and the instrument is actuated causing ejection of the staples and advancing movement of the annular knife through the tissue end margins supported by the cut ring and the backup member of the anvil head. Advancement of the annular knife causes the cut ring and the backup member to advance relative to the anvil housing and also to rotate through a predefined angular sector of rotation. The rotational movement of the cut ring and the backup member exerts a twisting action on the tissue captured by the annular knife, which in conjunction with the piercing action of the annular knife, provides a cutting effect on the tissue end margins that effectively severs and removes any excess tissue within the passage.

Figure 1:
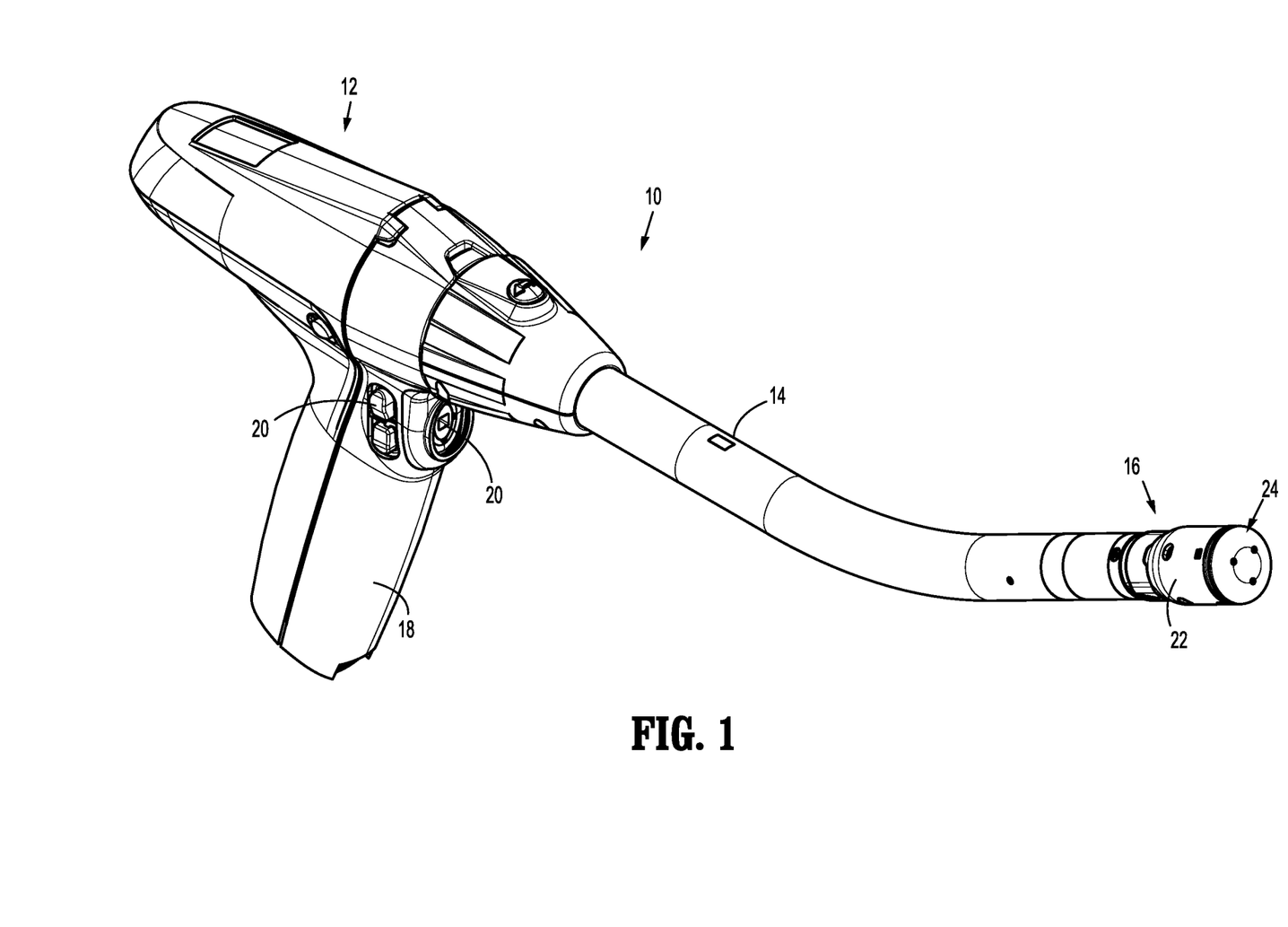
FIG. 1 is a perspective view of an exemplary embodiment of a surgical circular stapling instrument including the end effector and the anvil assembly of the present disclosure.
Figure 2:
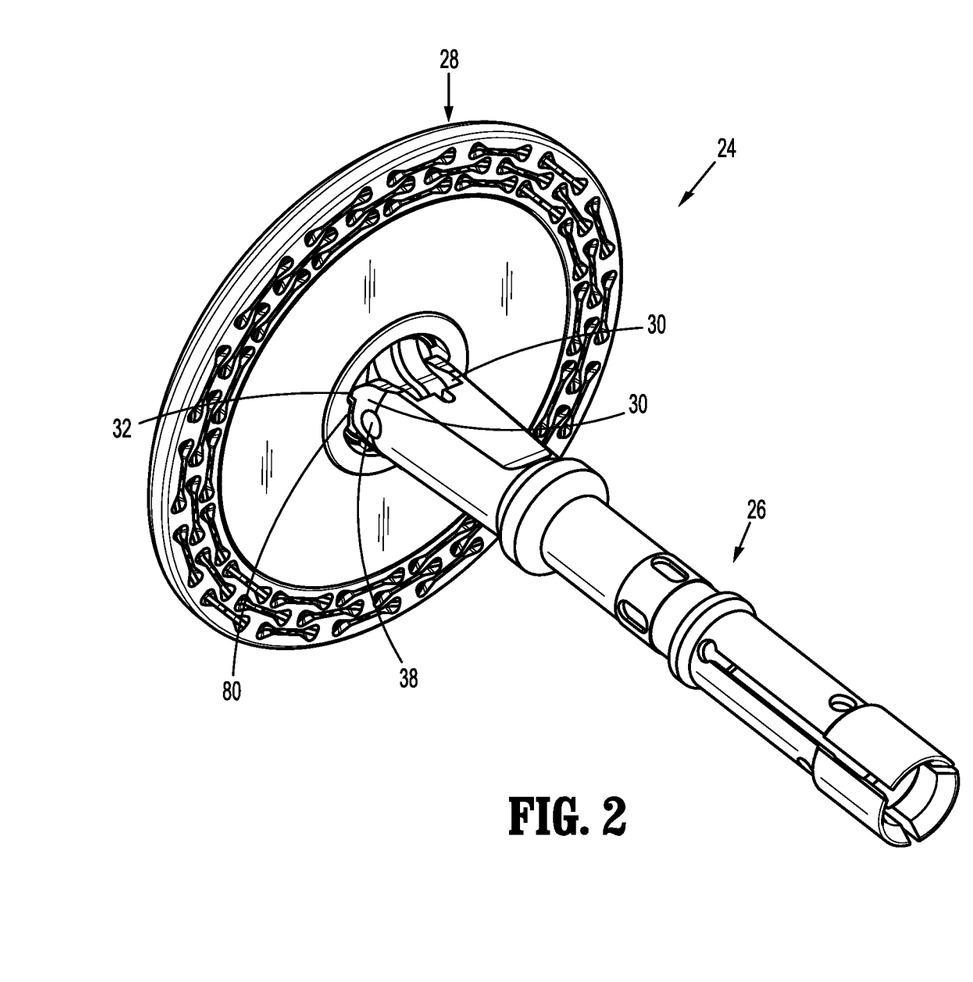
FIG. 2 is a perspective view of the anvil assembly of the end effector.

Referring to FIGS. 1-2, the circular stapling instrument incorporating the end effector of the present disclosure is illustrated and shown generally as circular stapling instrument 10. The circular stapling instrument 10 includes a handle 12, an elongate body or adapter 14 extending from the handle 12, and an end effector 16 coupled to the adapter 14. The handle 12 may be electrically powered including a motor and associated gears and linkages to control operation of the stapling instrument 10. The handle 12 incorporates a grip 18 and a plurality of actuation buttons 20 which may be activated to control various functions of the stapling instrument 10 including, e.g., approximation of the end effector 16 and firing of staples. The grip 18 may support a battery pack (not shown) which powers the handle 12.

In embodiments, the adapter 14 is releasably coupled to the handle 12 and includes a plurality of drive mechanisms (not shown) that translate power from the handle 12 to the end effector 16 in response to actuation of the actuation buttons 20 to effect operation, i.e., approximation and firing, of the end effector 16. Commonly assigned U.S. Pat. Nos. 9,247,940; 9,055,943; and 8,806,973; and U.S. Publication No. 2015/0014392 disclose exemplary embodiments of powered handles and adapters suitable for use with the stapling instrument 10, and which are incorporated in their respective entireties by reference herein. Alternately, the elongate body or adapter 14 can be non-removably secured to the handle 12. It is also envisioned that the handle 12 could be manually powered. Examples of manually powered handle assemblies are described in commonly assigned U.S. Pat. Nos. 8,789,737; 8,424,535; and 8,360,295, which are incorporated in their respective entireties by reference herein.

The end effector 16 includes a staple cartridge assembly 22 and an anvil assembly 24 couplable relative to the staple cartridge assembly 22. In general, the staple cartridge assembly 22 incorporates one or more annular rows of staples (not shown), staple pushers (not shown) for advancing the staples through the tissue end margins of the tubular organ sections and an annular knife (not shown in FIGS. 1-2)

internal of the staples to sever and remove excess organ tissue within the tubular organ sections upon advancement of the annular knife during, or subsequent to, deployment of the staples. The functioning of the annular knife will be discussed in detail hereinbelow.

Figure 3:
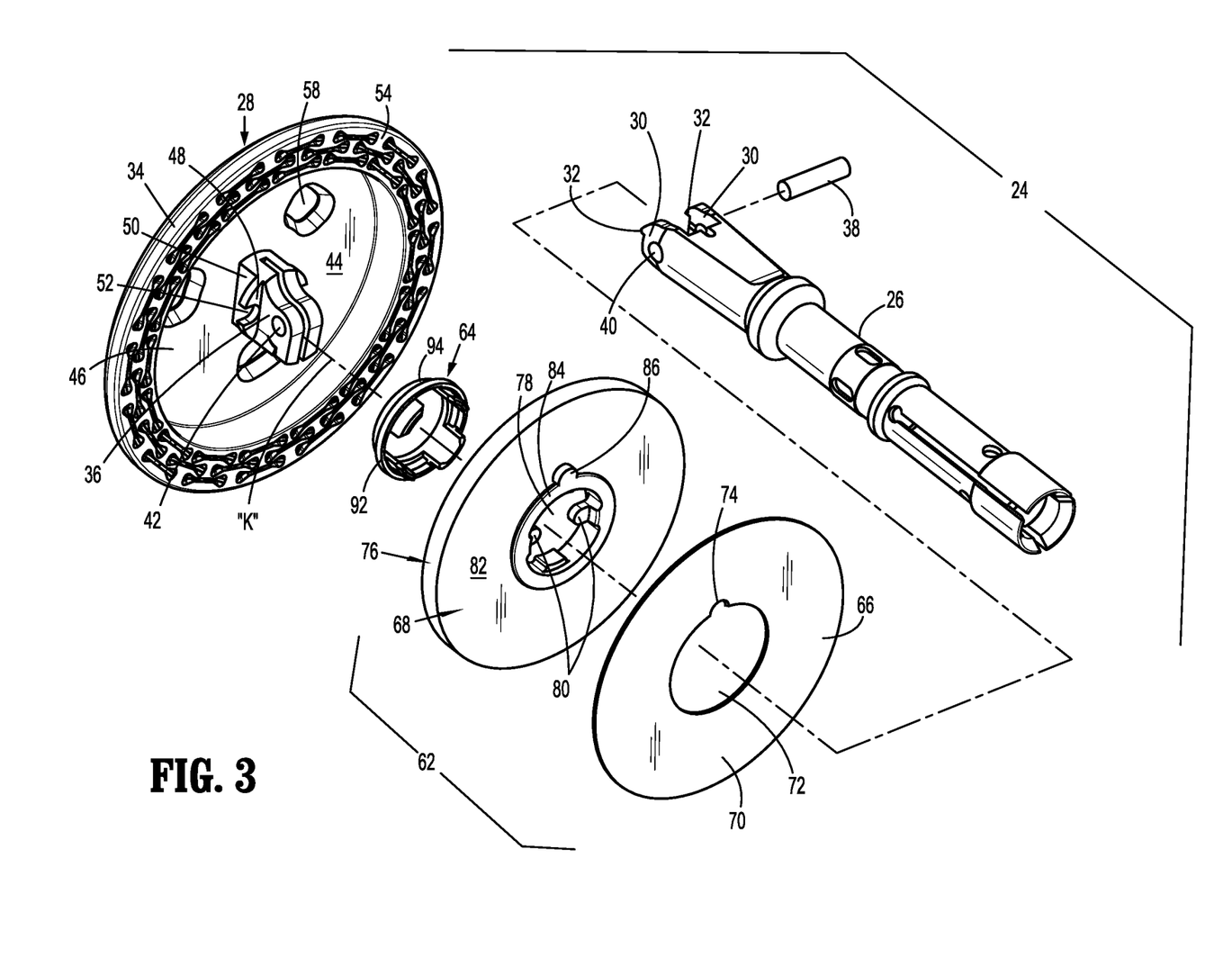
FIG. 3 is an exploded perspective view of the anvil assembly illustrating the anvil center rod, the support including the backup member and the cut ring, the retainer and the anvil head.

Referring now to FIGS. 2-3, the anvil assembly 24 of the end effector 16 will be discussed. The anvil assembly 24 shares some common features with the anvil assembly disclosed in commonly assigned U.S. Pat. No. 8,540,132, the entire contents of which are incorporated by reference herein. The anvil assembly 24 includes an anvil center rod 26 and an anvil head 28 pivotally mounted to the anvil center rod 26. The anvil center rod 26 includes a pair of spaced arms 30 with distal shelves 32. The anvil head 28 is adapted to pivot relative to the anvil center rod 26 between a first operative condition in opposition to the staple cartridge assembly (as depicted in FIG. 1) and a second pivoted or tilted condition, and may be normally biased to the second titled condition via a spring-biased plunger mechanism (not shown). The anvil head 28 includes an anvil housing 34 with an internal anvil post 36 which is at least partially received within the spaced arms 30 of the anvil center rod 26. A pivot pin 38 extends through respective transverse bores 40, 42 of the spaced arms 30 and the anvil post 36 to pivotally couple the anvil head 28 to the anvil center rod 26.

Figure 4:
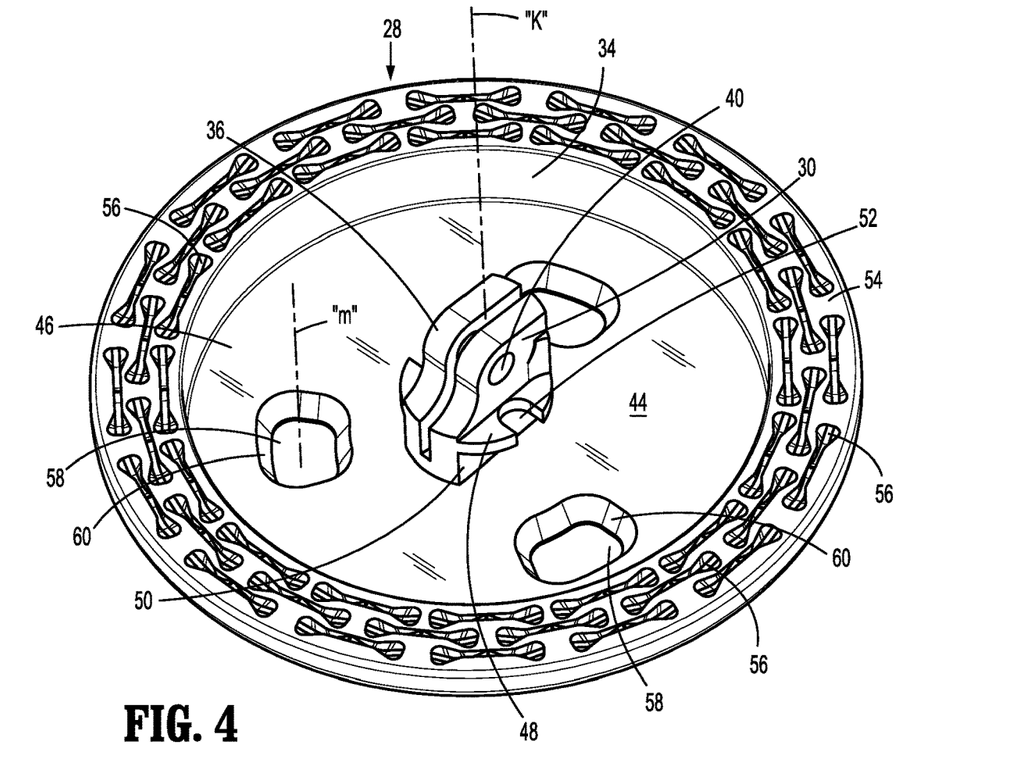
FIG. 4 is a perspective view of the anvil head illustrating the anvil housing, the anvil post for coupling with the anvil center rod and the cam recesses within the anvil housing.

With reference to FIGS. 3-4, the anvil housing 34 of the anvil assembly 24 defines a central longitudinal axis "k" along which the anvil post 36 extends. The anvil housing 34 includes a distal housing wall 44 which supports the anvil post 36, and an internal housing recess 46. The anvil post 36 includes a flange 48 spaced from the distal housing wall 44 to define a gap or clearance 50 between the flange 48 and the distal housing wall 44. The flange 48 includes at least one keyed slot 52 and, in embodiments, includes a pair of diametrically opposed keyed slots 52. The anvil housing 34 includes an outer tissue contact surface 54 circumscribing the internal housing recess 46. The outer tissue contact surface 54 supports the tissue end margins of a tubular organ section, and incorporates a plurality of staple deforming pockets 56 to receive and deform the staples ejected from the staple cartridge assembly 22.

The anvil housing 34 further includes a plurality of cam recesses 58 within the distal housing wall 44 and radially spaced relative to central longitudinal axis "k". The cam recesses 58 may extend partially through the distal housing wall 44 or, alternatively, completely through the distal housing wall 44 to define openings therethrough. The cam recesses 58 are defined by internal cam surfaces 60 which are obliquely arranged with respect to the central longitudinal axis "k". Three cam recesses 58 are depicted although more or less than three cam recesses 58 are contemplated. The cam recesses 58 may be equidistantly spaced relative to the central longitudinal axis "k" and relative to each other. Each cam recess 58 defines a centrally disposed recess axis "m".

With reference to FIG. 3, the anvil head 28 includes a support, generally identified as reference numeral 62, and a frangible or deformable retainer 64 distal of the support 62, each being disposed within the internal housing recess 46 of the anvil housing 34 coaxially arranged about the anvil post 36. The support 62 includes a cut ring 66 and a backup member 68, and is configured for longitudinal movement relative to the anvil housing 34 from an initial longitudinal position to an advanced longitudinal position upon movement of the annular knife toward its actuated position.

The cut ring 66 of the support 62 includes a disc-shaped annular body 70 defining a central aperture 72 for reception of the anvil post 36. The cut ring 66 further includes at least one keyed recess 74 adjacent the central aperture 72. The keyed recess 74 couples with corresponding structure of the backup member 68 such that rotational movement of the backup member 68 causes corresponding rotational movement of the cut ring 66. The cut ring 66 is at least partially penetrated by the annular knife during firing of the instrument 10 such that the tissue end margins overlying the cut ring 66 are severed by the annular knife to create a passage through the anastomosed tubular organ sections. In embodiments, the cut ring 66 is formed through a molding process, e.g., an injection molding process, and may be fabricated from a material having a durometer which permits the annular knife to pierce completely through the annular body 70 and bottom out against backup member 68. Suitable materials include polypropylene or polyester. Other materials are also contemplated.

Figure 5:
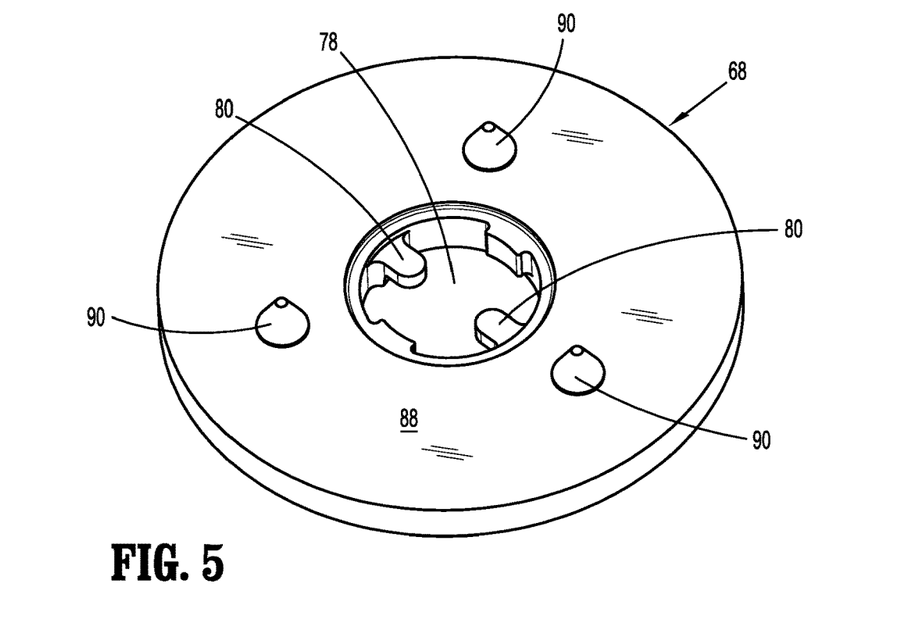
FIG. 5 is a perspective view of the backup member of the support illustrating the conical cam projections extending from a distal face of the backup member and the fingers extending inwardly within the central opening of the backup member.

With reference to FIGS. 3 and 5, the backup member 68 of the support 62 includes an outer plate segment 76 defining a central aperture 78 dimensioned for positioning about the anvil post 36 of the anvil housing 34. The backup member 68 includes a pair of diametrically opposed fingers 80 extending radially inwardly from the outer plate segment 76 and within the central aperture 78. The fingers 80 are received within the diametrically opposed keyed slots 52 of the flange 48 of the anvil post 36 to prevent rotational movement of the backup member 68 and the cut ring 66 about the central longitudinal axis "k" when the support 62 is in the initial longitudinal position. The fingers 80 also engage the distal shelves 32 of the spaced arms 30 of the anvil center rod 26 (FIG. 2) to prevent rotation of the anvil head 28 and maintain the anvil head 28 in an operative condition in opposition to the staple cartridge assembly 22. The proximal side 82 of the outer plate segment 76 includes a raised flange 84 (FIG. 3) which is received within the central aperture 72 of the cut ring 66. The raised flange 84 defines an outwardly projecting detent 86 which is received within the corresponding keyed recess 74 of the cut ring 66 to couple (e.g., rotatably couple) the backup member 68 to the cut ring 66. The raised flange 84 of the backup member 68 may be press fit within the central aperture 72 of the cut ring 66 to secure these components to each other. Alternatively, the backup member 68 and the cut ring 66 may be coupled with cements, adhesives, spot welding or the like.

Figure 6:
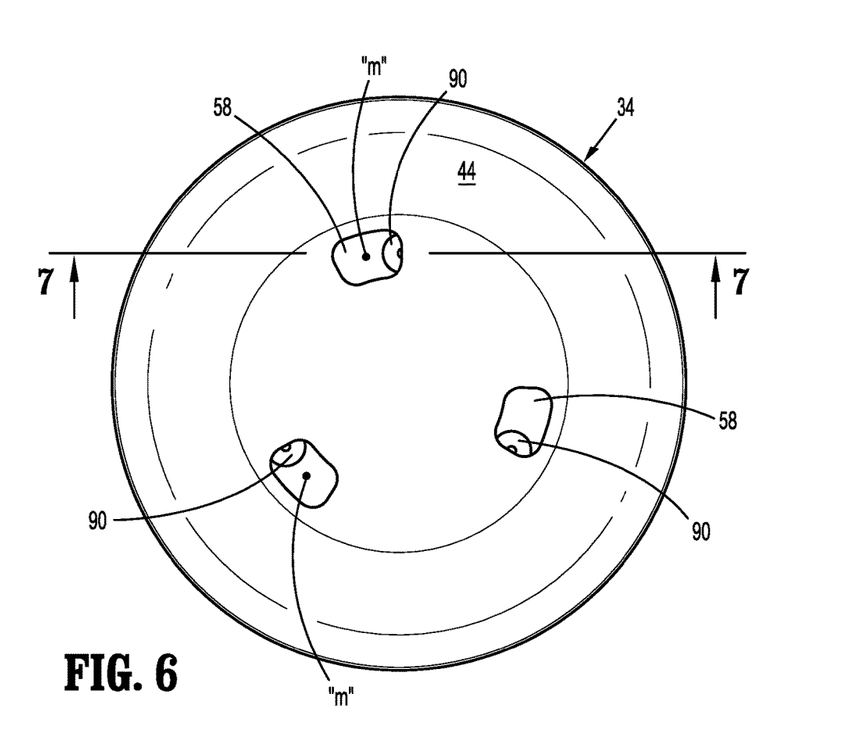
FIG. 6 is a top plan view of the anvil head illustrating the cam recesses extending through the anvil housing and the cam projections of the backup member in a first rotational orientation of the support relative to the anvil head.
Figure 7:
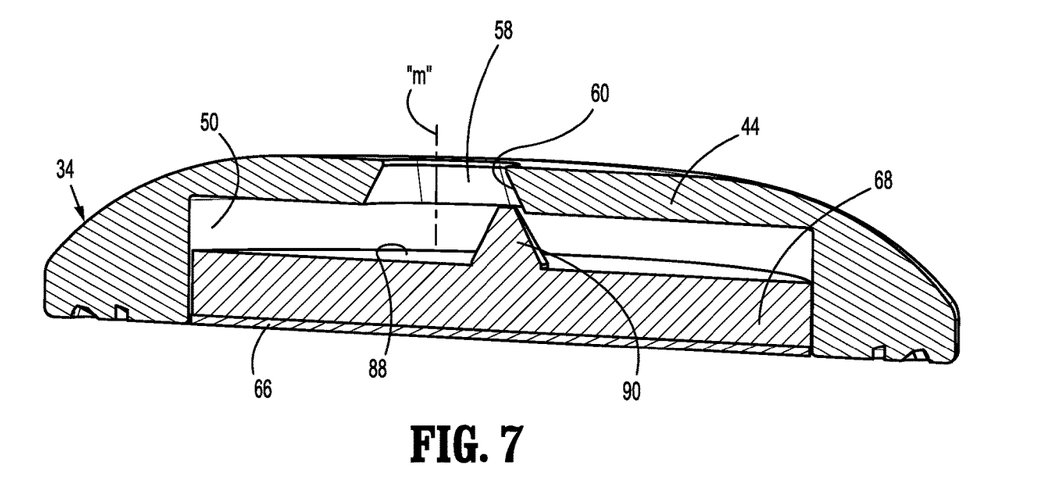
FIG. 7 is a cross-sectional view taken along the lines 7-7 of FIG. 6 illustrating the relationship of the cam projections of the backup member within the cam recesses of the anvil housing when in the first rotational orientation of the support.

With reference to FIGS. 5-7, the distal side 88 of the backup member 68 includes a plurality (e.g., three) of cam projections 90. More or less than three cam projections 90 are also contemplated. The cam projections 90 define a conical shape with a sloped outer surface although other configurations are envisioned. The cam projections 90 are radially spaced with respect to the central longitudinal axis "k" to at least partially align with the cam recesses 58 of the anvil housing 34 in the initial longitudinal position of the support 62 (FIGS. 6-7). In the initial longitudinal position of the support 62, the support 62 is in a first rotational orientation relative to the relative to the anvil housing 34 (FIG. 6). However, in the first rotational orientation of the support 62, the cam projections 90 are slightly askew, e.g., not perfectly aligned with the recess axes "m" of the respective cam recesses 58 of the distal housing wall 44, but rather are aligned to at least partially engage the internal cam surfaces 60 defining the cam recesses 58. The cam projections 90 cooperate with the internal cam surfaces 60 during advancement of the support 62, including the backup member 68 and the cut ring 66, to cause these components to rotate during actuation of the annular knife. This rotation causes the tissue captured between the annular knife and the cut ring 66 to twist about the annular knife which enhances the cutting action of the annular knife relative to the tissue. The backup member 68 may be formed from a hard material such as metal although other materials of construction are envisioned.

With reference again to FIG. 3, the retainer 64 is disposed about the anvil post 36 between the backup member 68 and the distal housing wall 44 of the anvil housing 34. The retainer 64 defines an outer flange 92 and a deformable or frangible annular member 94 distal of the outer flange 92. The annular member 94 is deformable upon application of a force thereto, e.g., during advancement of the annular knife of the end effector 16 during actuation of the annular knife. The annular member 94 defines an internal dimension less than the internal dimension of the outer flange 92 to permit the annular member 94 to deform and be at least partially received within the outer flange 92 upon actuation of the annular knife. The retainer 64 further includes a plurality of tabs 96 depending from the raised flange 84 in a proximal direction for reception within the central aperture 78 of the backup member 68. The tabs 96 stabilize the retainer 64 relative to the backup member 68.

Figure 8:
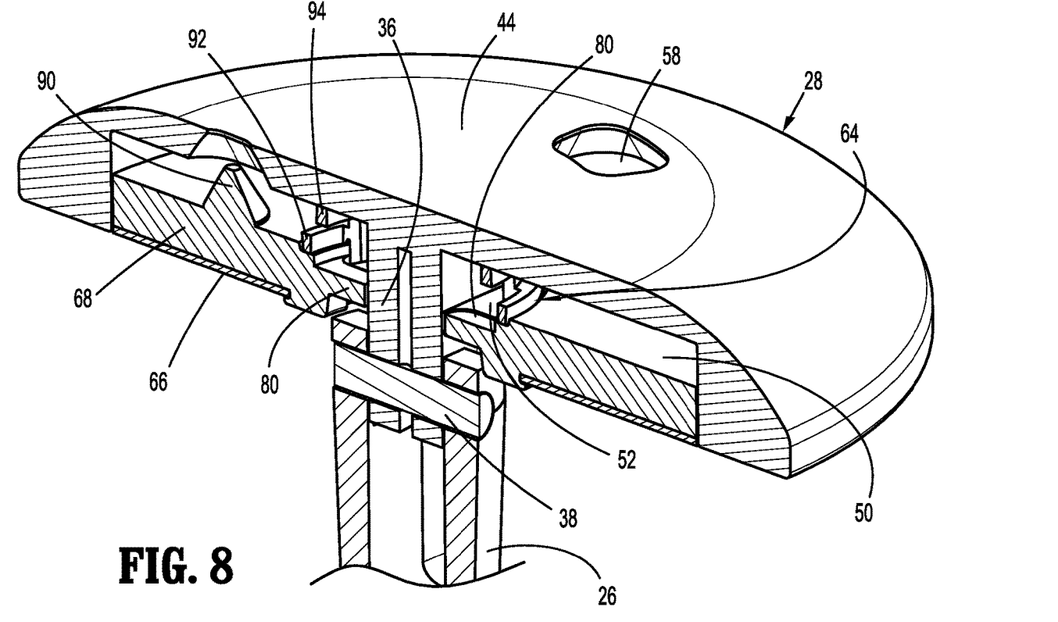
FIG. 8 is a perspective view in partial cross-section of the anvil head illustrating the retainer adjacent the anvil housing and the fingers of the backup member disposed within the key slots of the anvil post when in an initial longitudinal position of the support.

FIG. 8 illustrates the relationships of the components of the anvil assembly 24 prior to actuation of the annular knife and with the support 62, including the backup member 68 and the cut ring 66 in the initial longitudinal position. In the initial longitudinal position, the diametrically opposed fingers 80 of the backup member 68 are disposed within the opposed keyed slots 52 of the anvil post 36 to prevent rotational movement of the backup member 68 and the cut ring 66 about the central longitudinal axis "k". The retainer 64 is in engagement with the distal housing wall 44 and the backup member 68 to bias the backup member 68 and the cut ring 66 in a proximal direction corresponding to the initial longitudinal position of the support 62 and the operative condition of the anvil head 28.

Figure 9:
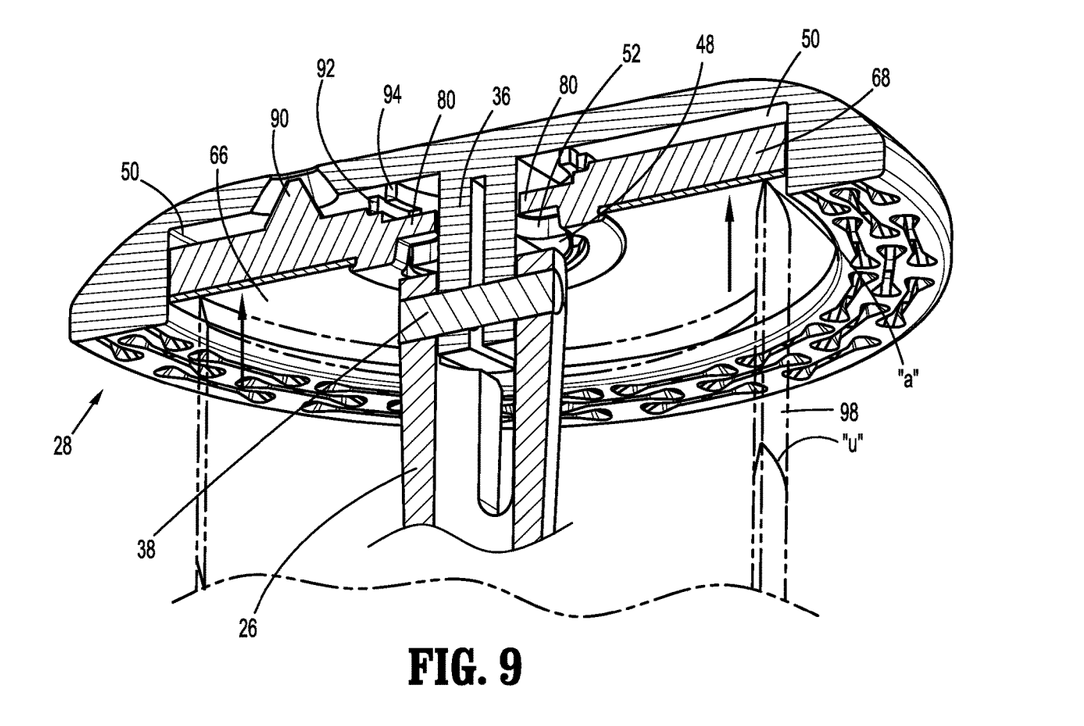
FIG. 9 is a perspective view in partial cross-section illustrating the annular knife of the end effector advanced to drive the backup member and the cut ring against the retainer and toward the anvil housing corresponding to an advanced longitudinal position of the support.

The use of the end effector 16 will now be discussed. The tissue end margins of the tubular organ sections to be joined are placed about the anvil head 28 and the staple cartridge assembly 22, respectively and secured via a purse string stitch or any other conventional methodology. The anvil head 28 and the staple cartridge assembly 22 are approximated. The stapling instrument 10 is then fired to eject the staples from the staple cartridge assembly 22 for passage through the tissue end margins of the tubular organ sections and deformation against the staple receiving pockets 56 of the anvil housing 3. With reference to FIG. 9, the annular knife 98 is actuated to advance the annular knife 98 from an unactuated position (shown in phantom as "u" in FIG. 9) within the staple cartridge assembly 22 (not shown) to an actuated position "a" extending through the tissue end margins and at least partially or completely through the cut ring 66 of the support 62. As the annular knife 98 engages the cut ring 66, the cut ring 66 and the backup member 68 are advanced toward the advanced longitudinal position of the support 62. This motion causes the backup member 68 to exert a force on the retainer 64 sufficient to cause deformation of the annular member 94 of the retainer 64 such that the annular member 94 is received within the outer flange 92 of the retainer 64. The deformation of the retainer 64 also permits the support 62, including the backup member 68 and the cut ring 66, to advance within the gap 50 defined between the flange 48 of the anvil post 36 and the distal housing wall 44 of the anvil housing 34. In this position, the fingers 80 of the backup member 68 are released from the keyed slots 52 of the anvil post, i.e., the fingers 80 are distal of the flange 48 and the keyed slots 52 thereby freeing the backup member 68 and the cut ring 66 for rotation about the central longitudinal axis "k".

Figure 10:
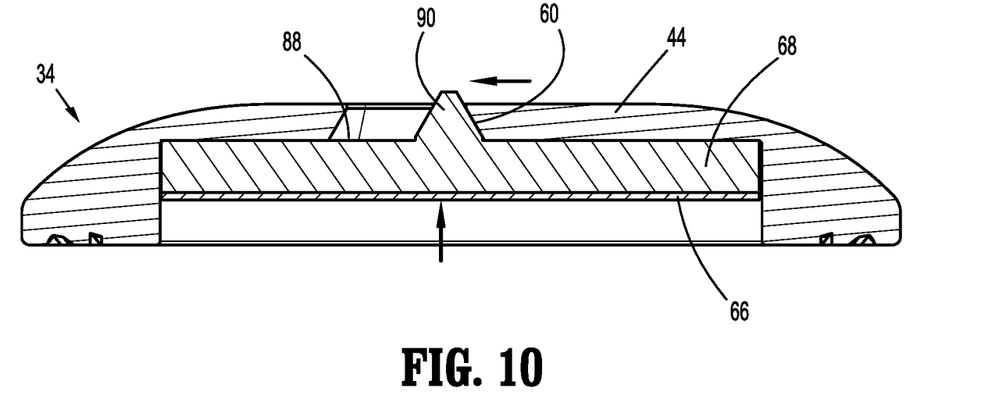
FIG. 10 is a view similar to the view of FIG. 7 illustrating the cam projections of the backup member advanced within the cam openings of the anvil housing to cause rotational movement of the support to a second rotational orientation relative to the anvil head.
Figure 11:
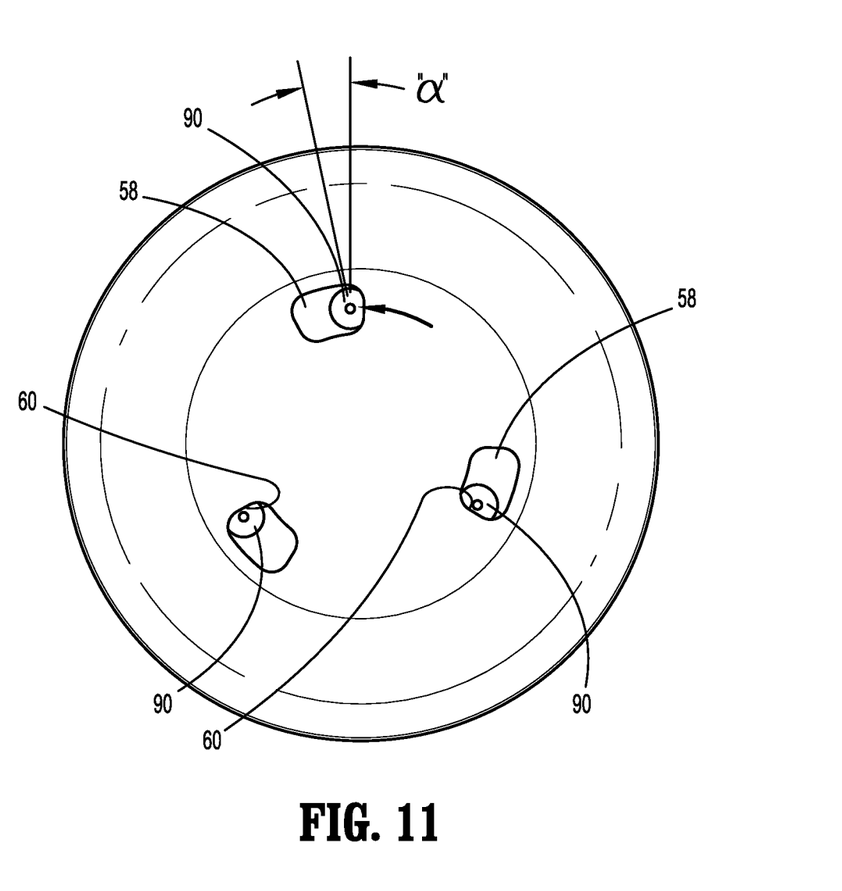
FIG. 11 is a top plan view of the anvil head similar to the view of FIG. 6 illustrating the support in the second rotational orientation with the cam projections of the backup member extending within the cam recesses of the anvil housing.

As best depicted in FIGS. 10-11, simultaneously with the advancing movement of the support 62 toward its advanced longitudinal position, the cam projections 90 on the distal side 88 of the backup member 68 engage the internal cam surfaces 60 defining the cam recesses 58 of the distal housing wall 44 of the anvil housing 34 to cause the support 62, including the backup member 68 and the coupled cut ring 66, to rotate through a pre-determined angular sector of rotation "a" from the first rotational orientation relative to the anvil housing 34 (FIG. 6) to a second rotational orientation relative to the anvil housing 34 (FIG. 11). This rotation causes the tissue engaged between the cut ring 66 and the annular knife 98 to twist about the annular knife 98. The twisting action coupled with the longitudinal advancement of the annular knife 98 through the tissue and through the cut ring 66 effectively removes, e.g., through a coring action, any organ tissue within the passage of the connected tubular organs. The predetermined angular sector of rotation "a" may be relatively small to impart a slight twisting motion to the support 62 or may be relatively large to impart a substantial twisting motion to the tissue. For example, the predetermined angular sector of rotation "a" may range between 1° and 360°. In embodiments, the predetermined angular sector of rotation "a" is less than 10°. This slight twisting motion is sufficient to release the captured organ tissue and provide a clear passage through the anastomosed organ sections.

Figure 12:
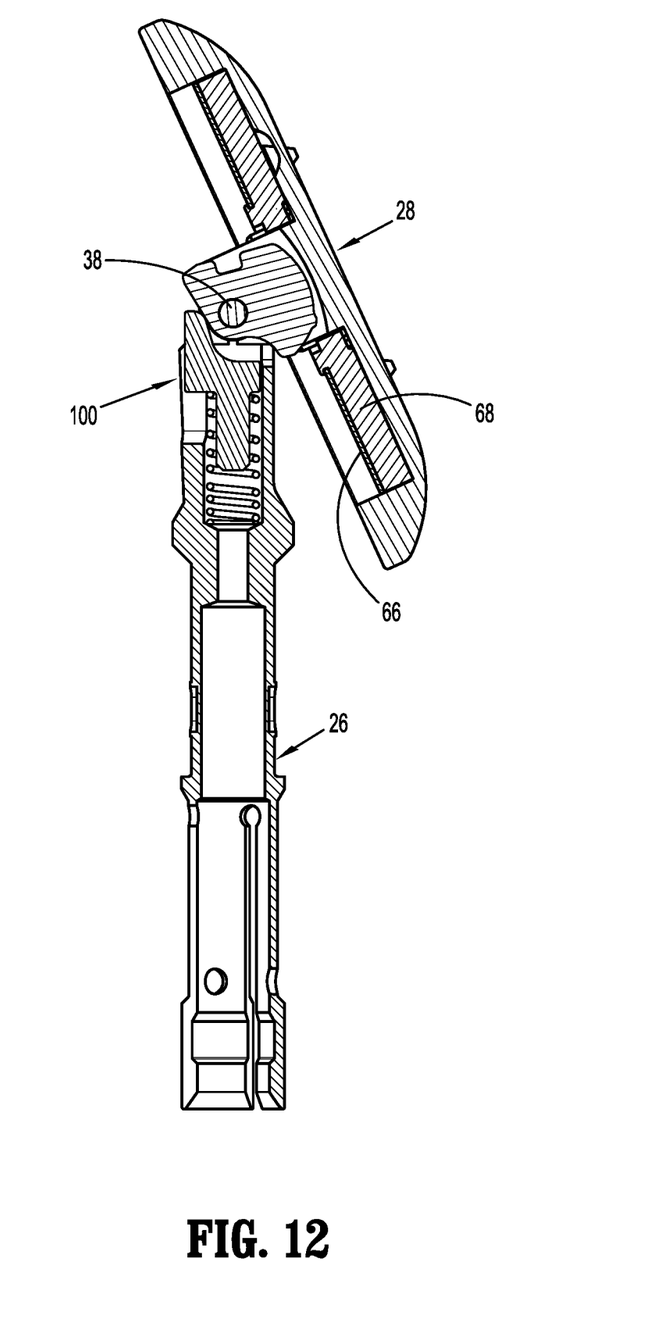
FIG. 12 is a cross-sectional view of the anvil head in a tilted condition relative to the anvil center rod.

With the support 62 in the advanced longitudinal position, the fingers 80 of the backup member 68 are released from the distal shelves 32 of the spaced arms 30 of the anvil center rod 26. Thus, the anvil head 28 may pivot from the first operative condition in which the anvil head 28 is in opposition to the staple cartridge assembly 22 (FIG. 1) to a second tilted condition depicted in FIG. 12. A spring biased plunger mechanism, identified generally as reference numeral 100, associated with the anvil center rod 26 will cause the anvil head 28 to pivot about the pivot member 38 to assume the second tilted condition depicted in FIG. 12. Details of the plunger mechanism may be ascertained by reference to U.S. Pat. No. 8,540,132.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. For example, the cut ring 66 and the backup member 68 of the support 62 may be a single unit. Alternatively, the support 62 may be only inclusive of the backup member 68. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. An end effector for use with a circular stapling instrument, comprising:
    a staple cartridge assembly including an annular knife, the annular knife configured for advancing movement from an unactuated position to an actuated position; and
    an anvil assembly mountable relative to the staple cartridge assembly, the anvil assembly including:
        an anvil center rod; and an anvil head coupled to the anvil center rod, the anvil head including:
  an anvil housing defining a central longitudinal axis; and
  a support disposed within the anvil housing, the support configured for longitudinal movement relative to the anvil housing from an initial longitudinal position to an advanced longitudinal position upon movement of the annular knife toward the actuated position, the support configured to rotate through a predetermined angular sector of rotation about the central longitudinal axis upon movement to the advanced longitudinal position to facilitate severing of tissue disposed between the annular knife and the support.

2. The end effector according to claim 1, wherein the support includes a backup member, the backup member having at least one cam member engageable with the anvil housing to cause rotation of the support through the predetermined angular sector of rotation.

3. The end effector according to claim 2, wherein the anvil housing includes a distal housing wall, the housing wall having at least one cam recess, the at least one cam member of the backup member cooperating with the at least one cam recess to cause rotation of the support through the predetermined angular sector of rotation.

4. The end effector according to claim 3, wherein the backup member includes a plurality of cam members depending from a distal face thereof.

5. The end effector according to claim 4, wherein the housing wall of the anvil housing defines a plurality of cam recesses, individual cam members of the plurality of cam members cooperating with respective individual cam recesses of the plurality of cam recesses to rotate the support through the predetermined angular sector of rotation.

6. The end effector according to claim 5, wherein the plurality of cam members of the backup member and the plurality of cam recesses of the housing wall of the anvil housing are radially spaced with respect to the central longitudinal axis.

7. The end effector according to claim 3, wherein the support includes a cut ring, the cut ring positioned to be engaged by the annular knife upon movement of the annular knife toward the actuated position.

8. The end effector according to claim 7, wherein the cut ring is coupled to the backup member such that rotation of the backup member causes corresponding rotation of the cut ring.

9. The end effector according to claim 8, wherein the cut ring is configured to be at least partially penetrated by the annular knife upon movement of the annular knife toward the actuated position.

10. The end effector according to claim 9, wherein the anvil head is pivotally mounted to the anvil center rod, and is pivotal from a first operative condition in which the anvil head is in opposition to the staple cartridge assembly to a second tilted condition.

11. The end effector according to claim 8, including a retainer member positioned in the anvil housing between the backup member and the housing wall, the retainer member configured to deform when subjected to a force exerted by the annular knife on the support upon movement of the annular knife to the actuated position thereby permitting longitudinal advancement of the support to the advanced longitudinal position.

12. The end effector according to claim 11, wherein the support is fixed from rotational movement about the central longitudinal axis when in the initial longitudinal position.

13. The end effector according to claim 12, wherein the anvil head includes an anvil post depending from the housing wall, wherein the retainer, the backup member and the cut ring are coaxially mounted about the anvil post.

14. The end effector according to claim 13, wherein the anvil post includes at least one keyed slot and the backup member includes a corresponding at least one finger, the at least one finger being received within the at least one keyed slot when in the initial longitudinal position of the support thereby preventing rotational movement of the support, and being released from the at least one keyed slot when in the advanced longitudinal position of the support thereby permitting rotational movement of the support.

15. The end effector according to claim 14, wherein the anvil post includes a pair of diametrically opposed keyed slots and the backup member includes a pair of corresponding diametrically opposed fingers.

16. An anvil assembly comprising:
  an anvil center rod defining a central longitudinal axis; and
  an anvil head coupled to the anvil center rod, the anvil head including:
    an anvil housing defining a central longitudinal axis; and
    a support disposed within the anvil housing, the support configured for longitudinal movement relative to the anvil housing from an initial longitudinal position to an advanced longitudinal position, the support configured to rotate through a predetermined angular sector of rotation about the central longitudinal axis upon movement of the support to the advanced longitudinal position to facilitate severing of tissue disposed on the support.

17. The anvil assembly according to claim 16, wherein the support includes a backup member, the backup member having at least one cam member engageable with the anvil housing to cause rotation of the support through the predetermined angular sector of rotation.

18. The anvil assembly according to claim 17, wherein the anvil housing includes a distal housing wall, the distal housing wall having at least one cam recess, the at least one cam member of the backup member cooperating with the at least one cam recess to cause rotation of the support through the predetermined angular sector of rotation.

19. The end effector according to claim 18, wherein the backup member includes a distal face and the at least one cam member includes a plurality of cam members that depend from the distal face, the housing wall of the anvil housing defining a plurality of cam recesses, wherein individual cam members of the plurality of cam members cooperate with respective individual cam recesses of the plurality of cam recesses to rotate the support through the predetermined angular sector of rotation.

20. The end effector according to claim 19, wherein the plurality of cam members of the backup member and the plurality of cam recesses of the housing wall of the anvil housing are radially spaced with respect to the central longitudinal axis.

* * * * *